(12) United States Patent
Newell et al.

(10) Patent No.: US 8,906,846 B2
(45) Date of Patent: Dec. 9, 2014

(54) METHOD OF TREATING INFLAMMATORY BOWEL DISEASE BY ADMINISTERING A CLIP-INDUCING AGENT

(75) Inventors: Martha Karen Newell, Holland, TX (US); Cassie L. Harvey, Salado, TX (US); Richard Tobin, Aurora, CO (US)

(73) Assignees: The Texas A&M University System, College Station, TX (US); Scott & White Healthcare, Temple, TX (US)

( * ) Notice: Subject to any disclaimer, the term of this patent is extended or adjusted under 35 U.S.C. 154(b) by 0 days.

(21) Appl. No.: 13/977,944

(22) PCT Filed: Jan. 5, 2012

(86) PCT No.: PCT/US2012/020332
§ 371 (c)(1),
(2), (4) Date: Jul. 2, 2013

(87) PCT Pub. No.: WO2012/094495
PCT Pub. Date: Jul. 12, 2012

(65) Prior Publication Data
US 2013/0295047 A1  Nov. 7, 2013

Related U.S. Application Data

(60) Provisional application No. 61/429,852, filed on Jan. 5, 2011.

(51) Int. Cl.
| A61K 38/00 | (2006.01) |
| A61K 45/00 | (2006.01) |
| A61K 38/08 | (2006.01) |
| A61K 48/00 | (2006.01) |
| A61K 31/7088 | (2006.01) |
| A61K 38/20 | (2006.01) |
| A61K 38/16 | (2006.01) |
| A61K 38/17 | (2006.01) |

(52) U.S. Cl.
CPC ............. *A61K 38/08* (2013.01); *A61K 31/7088* (2013.01); *A61K 38/2026* (2013.01); *A61K 38/16* (2013.01); *A61K 38/1774* (2013.01)
USPC .......... 514/1.1; 424/85.2; 514/21.8; 514/44 R

(58) Field of Classification Search
CPC ... A61K 38/03; A61K 38/17; A61K 38/1774; A61K 38/2026; A61K 2300/00; C07K 4/12; C07K 14/35; C07K 14/5406; C07K 14/70578
See application file for complete search history.

(56) References Cited

U.S. PATENT DOCUMENTS

| 6,326,465 B1 | 12/2001 | Hess |
| 7,312,318 B2 | 12/2007 | Hansen et al. |
| 8,557,764 B2 * | 10/2013 | Newell et al. .................. 514/3.8 |
| 2009/0175838 A1 * | 7/2009 | Newell Rogers et al. . 424/93.71 |
| 2010/0034839 A1 | 2/2010 | Newell et al. |
| 2010/0166782 A1 | 7/2010 | Newell et al. |
| 2010/0166789 A1 | 7/2010 | Keledjian et al. |
| 2011/0118175 A1 | 5/2011 | Newell et al. |
| 2013/0259829 A1 | 10/2013 | Newell et al. |
| 2014/0220000 A1 | 8/2014 | Newell et al. |

FOREIGN PATENT DOCUMENTS

WO    WO 97/25344 A1    7/1997

OTHER PUBLICATIONS

Adams et al., Biological activity and therapeutic potential of homologs of an Ii peptide which regulates antigenic peptide binding to cell surface MHC class II molecules. Arzneimittelforschung. Sep. 1997;47(9):1069-77.
Barrera et al., The role of the invariant chain in mucosal immunity. Int Arch Allergy Immunol. Oct. 1998;117(2):85-93.
Bretscher et al., A theory of self-nonself discrimination. Science. Sep. 11, 1970;169(950):1042-9.
Burrows et al., A murine model for antibody-directed targeting of vascular endothelial cells in solid tumors. Cancer Res. Nov. 1, 1992;52(21):5954-62.
Calabrese et al., Biochemical alterations from normal mucosa to gastric cancer by ex vivo magnetic resonance spectroscopy. Cancer Epidemiol Biomarkers Prev. Jun. 2008;17(6):1386-95.
Carrel et al., Recombinant interferon-gamma can induce the expression of HLA-DR and -DC on DR-negative melanoma cells and enhance the expression of HLA-ABC and tumor-associated antigens. Eur J Immunol. Feb. 1985;15(2):118-23.
Castellino et al., Antigen presentation by MHC class II molecules: invariant chain function, protein trafficking, and the molecular basis of diverse determinant capture. Hum Immunol. May 1997;54(2):159-69. Review.
Chaturvedi et al., The functional role of class II-associated invariant chain peptide (CLIP) in its ability to variably modulate immune responses. Int Immunol. Jun. 2000;12(6):757-65.
Cheng, A novel immunotherapeutic for cancer and autoimmune diseases. Drug Disc Devel. Feb. 22, 2012. Last accessed online via http://www.dddmag.com/articles/2012/02/novel-im-munotherapeutic-cancer-and-autoimm ... on Nov. 19, 2012. 5 pages.
Cosgrove et al., Mice lacking MHC class II molecules. Cell. Sep. 6, 1991;66(5):1051-66.
Frölich et al., the anti-CD74 humanized monoclonal antibody, milatuzumab, which targets the invariant chain of MHC II complexes, alters B-cell proliferation, migration, and adhesion molecule expression. Arthritis Res Ther. Mar. 9, 2012;14(2):R54. doi:10.1186/ar3767.
Gunther et al., Bidirectional binding of invariant chain peptides to an MHC class II molecule. Proc Natl Acad Sci U S A. Dec. 21, 2010;107(51):22219-24. Epub Nov. 29, 2010.

(Continued)

*Primary Examiner* — Robert Landsman

(57) ABSTRACT

The disclosure relates to methods for treating disorders of the mucosal tract such as the gastrointestinal system by targeting CLIP molecules. The methods are based on that CLIP in the groove of MHC class I or II molecules of the cells lining the mucosal surfaces of the body, such as the gastrointestinal tract, provides protection from MHC Class II or MHC class I mediated cell death, and therefore are useful for treating, inhibiting the development of a multitude of illnesses and conditions of the mucosal tract, including autoimmune disease.

8 Claims, 4 Drawing Sheets

(56) References Cited

OTHER PUBLICATIONS

Hillman et al., Generating MHC Class II+/Ii- phenotype after adenoviral delivery of both an expressible gene for MHC Class II inducer and an antisense Ii-RNA construct in tumor cells. Gene Ther. Aug. 2003;10(17):1512-8.

Hitzel et al., The invariant chain derived fragment CLIP is an efficient in vitro inhibitor of peptide binding to MHC class II molecules. Mol Immunol. Jan. 1996;33(1):25-31.

Kasai et al., CLIP-derived self peptides bound to MHC class II molecules of medullary thymic epithelial cells differ from those of cortical thymic epithelial cells in their diversity, length, and C-terminal processing. Eur J Immunol. Dec. 2000;30(12):3542-51.

Matsushita et al., HLA-DR antigen expression in colorectal carcinomas: influence of expression by IFN-gamma in situ and its association with tumour progression. Br J Cancer. Mar. 1996;73(5):644-8.

Matza et al., Invariant chain, a chain of command. Trends Immunol. May 2003;24(5):264-8.

Newell et al., Does the oxidative/glycolytic ratio determine proliferation or death in immune recognition? Ann N Y Acad Sci. 1999;887:77-82. Review.

Newell et al., Ligation of major histocompatibility complex class II molecules mediates apoptotic cell death in resting B lymphocytes. Proc Natl Acad Sci U S A. Nov. 15, 1993;90(22):10459-63.

Newell et al., Regulation of Immune Responses by Cell Death. *When Cells Die*. Wiley, Liss, and Co. Publishers, 1998:268-277.

Newell et al., TLR-mediated B cell activation results in ectopic Clip expression that promotes B cell-dependent inflammation. J Leukoc Biol. Oct. 2010;88(4):779-89. Epub Jul. 14, 2010.

Newell, Transmembrane signaling through major histocompatability complex (MCH) encoded molecules, 1987, University of Colorado Health Services Center, Denver, CO.

Newell et al., Studies with glycolysis-deficient cells suggest that production of lactic acid is not the only cause of tumor acidity. Proc Natl Acad Sci U S A. Feb. 1, 1993;90(3):1127-31.

Nowell et al., Chloroquine affects biosynthesis of Ia molecules by inhibiting dissociation of invariant (gamma) chains from alpha-beta dimers in B cells. J Exp Med. Oct. 1, 1985;162(4):1371-6.

Powis, CLIP-region mediated interaction of Invariant chain with MHC class I molecules. FEBS Lett. May 29, 2006;580(13):3112-6. Epub Apr. 27, 2006.

Röhn et al., Upregulation of the CLIP self peptide on mature dendritic cells antagonizes T helper type 1 polarization. Nat Immunol. Sep. 2004;5(9):909-18.

Schweitzer et al., Endogenous versus exogenous fatty acid availability affects lysosomal acidity and MHC class II expression. J Lipid Res. Nov. 2006;47(11):2525-37. Epub Aug. 16, 2006.

Stumptner et al., Interaction of MHC class II molecules with the invariant chain: role of the invariant chain (81-90) region. EMBO J. Oct. 1, 1997;16(19):5807-18.

Truman et al., HLA class II signaling mediates cellular activation and programmed cell death. Exp Hematol. Oct. 1996;24(12):1409-15.

Wu et al., the MHC class II-associated invariant chain-derived peptide clip binds to the peptide-binding groove of class II molecules. Mol Immunol. Mar.-Apr. 1996;33(4-5):371-7.

Xu et al., Immunotherapy of cancer by antisense inhibition of Ii protein, an immunoregulator of antigen selection by MHC class II molecules. Curr Opin Mol Ther. Apr. 2004;6(2):160-5.

Zinkernagel et al., The discovery of MHC restriction. Immunol Today. Jan. 1997;18(1):14-7.

\* cited by examiner

US 8,906,846 B2

METHOD OF TREATING INFLAMMATORY BOWEL DISEASE BY ADMINISTERING A CLIP-INDUCING AGENT

RELATED APPLICATIONS

This application is a national stage filing under U.S.C. §371 of PCT International application PCT/US2012/020332, filed Jan. 5, 2012, which was published under PCT Article 21(2) in English. Application PCT/US2012/020332 claims priority under 35 U.S.C. §119(e) to U.S. Provisional Application Ser. No. 61/429,852, entitled "CLIP MODULATION FOR THE TREATMENT OF MUCOSAL DISEASES" filed on Jan. 5, 2011, which is herein incorporated by reference in its entirety.

BACKGROUND OF INVENTION

The immune system consists of innate and adaptive or acquired immune responses. The innate immune response is immediate and includes physical, chemical or mechanical barriers, along with cells that are the first to the site of infection or damage, the neutrophils, followed by dendritic cells and macrophages, all of which can engulf or phagocytize potentially harmful pathogens or debris. The phagocytes also are involved in the transition between innate and acquired immunity by processing and loading their engulfed material, loading the fragments into molecules that are embedded in the lysosomal/endosomal compartments, the Major and Minor Histocompatibility Complex (MHC) encoded molecules of T cell immunity. MHC is believed to be the genetic complex responsible for the rejection. The MHC genes, also known as immune response or IR genes, and their protein products are responsible for all graft rejection. There are two types of MHC molecules: MHC class I and MHC class II. All nucleated cells express cell surface MHC class I. A subset of specialized cells express class II MHC. Included in the specialized, professional antigen-presenting cells (APCs) are B cells, macrophages, microglia, dendritic cells, and Langerhans cells among others.

B lymphocytes are specialized cells with specific receptors that are antigen specific that ultimately secrete a soluble copy of its membrane-bound antigen receptor. Once antigen has been bound by the antigen receptor on the B cell, the antigen and its receptor are engulfed into an endosomal compartment. This compartment fuses with another compartment known as the lysosome. The B cell is very efficient at breaking down antigens into smaller parts and loading the parts into MHC class II in the lysosome. The MHC is then trafficked to the cell surface where the B cell can effectively "show" the antigen to a CD4+ T cell. The activated CD4 cell is also called a helper cell and there are two major categories, Th1 and Th2.

The MHC molecules are tightly protected in the endosomal/lysosomal compartments to insure that only antigens for which we need a response get presented to T cells. MHC class II molecules, prior to antigen loading, are associated with a peptide fragment derived from a molecule called invariant chain, also known as CD74. The invariant chain is associated with MHC class II (and recently shown to be associated with certain MHC class I molecules) prior to antigen loading into the antigen binding grooves of the MHC molecules. As antigen is processed, the invariant chain gets cleaved by proteases within the compartment. First an end piece is removed, and then another known as CLIP (class II invariant chain associated peptide). CLIP fills the groove that will ultimately hold the antigen until the antigen is properly processed. For a detailed review of the invariant chain, including CLIP, see Matza et al. (2003), incorporated herein in its entirety. Despite the fact that this "chaperone" role for invariant chain and CLIP has been identified, the full impact of these molecules on immune signaling and activation has yet to be determined.

SUMMARY OF INVENTION

The invention is based at least in part on the discovery that CLIP on the cell surface provides a protective "armor" for a cell expressing cell surface CLIP and that CLIP in the groove of MHC class I or II molecules of the cells lining the mucosal surfaces of the body, such as the gastrointestinal tract, as well as the endothelium, not only prevents T cell recognition, but also provides protection from MHC Class II or MHC class I mediated cell death. We demonstrate herein that CLIP in the groove of MHC class II can directly prevent MHC-mediated cell death. Therefore agents that promote CLIP on MHC expressing cells, including exogenous CLIP, are useful in the treatment of mucosal system disorders such as gastrointestinal disorders, for instance, autoimmune disease gastrointestinal cellular damage resulting from infectious disease.

The invention in some aspects is a method of protecting a mucosal cell, for instance a gastrointestinal cell, from MHC class I or MHC class II-mediated cell death by contacting a mucosal cell with a CLIP inducing agent in an effective amount to place CLIP peptide on the mucosal cell surface and protect the mucosal cell from MHC class I or MHC class II-mediated cell death. The mucosal cell may be a gastrointestinal cell. In some embodiments the mucosal cell may be an epithelial cell or an endothelial cell, for instance. In some embodiments the CLIP inducing agent is exogenous CLIP. The exogenous CLIP may be an amino acid sequence comprising a region consisting essentially of SEQ ID NO:1 (Met Arg Met Ala Thr Pro Leu Leu Met).

In other aspects a method of treating a subject having an autoimmune disease of the gastrointestinal tract is provided. The method involves orally administering to the subject a CLIP inducing agent in an effective amount to treat the autoimmune disease. In some embodiments the autoimmune disease is Crohn's disease, ulcerative colitis, or celiac disease. In other embodiments the CLIP inducing agent is exogenous CLIP. The exogenous CLIP may be an amino acid sequence comprising a region consisting essentially of SEQ ID NO:1. In yet other embodiments the CLIP inducing agent is a CLIP expression vector or is a CLIP activator selected from the group consisting of palmitoylated protein or PAM and an anti-CD40 or CD40L molecule in combination with IL-4.

A method of treating a subject having a disorder of the mucosal tract is provided according to other aspects of the invention. The method involves mucosally administering to the subject a CLIP inducing agent in an effective amount to treat the disorder. In some embodiments the disorder of the mucosal tract is a disorder of the gastrointestinal tract and is caused by *H. pylori* infection or HIV infection.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing,"

"involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
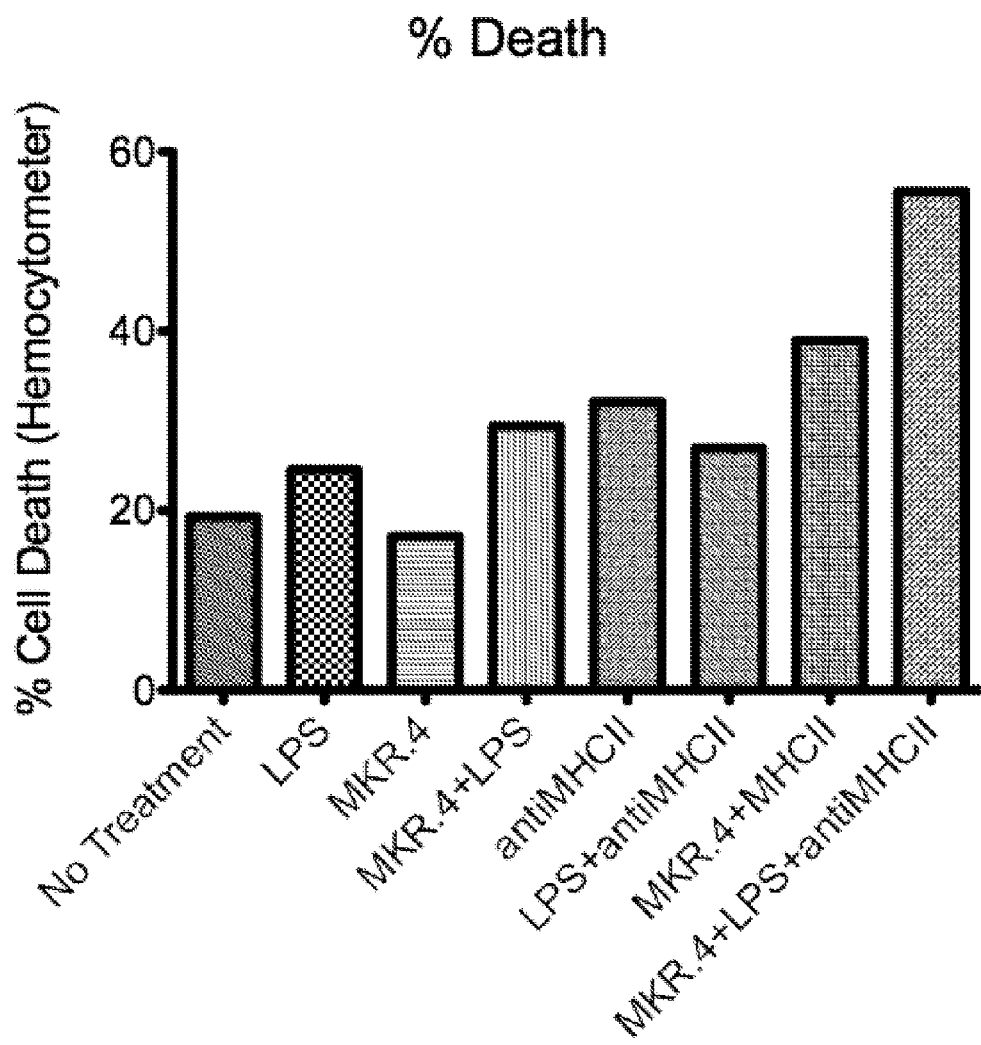
FIG. 1 depicts % cell death in either untreated human gastrointestinal epithelial cells or cells treated with LPS, MKR.4, MKR.4+LPS, anti-MHC class II antibody, LPS+anti-MHC class II antibody, MKR.4+anti-MHC class II antibody or MKR.4+LPS+anti-MHC class II antibody.

When a B cell is activated non-specifically, we previously discovered that the B cell expresses an important, small self-peptide called MHC class II invariant peptide, CLIP. In most individuals, a control cell, known as a T regulatory cell (Treg for short), has been shown, to kill the activated B cell. If naïve B cell MHC molecules are engaged prior to B cell antigen receptor engagement, the consequence for the B cell is cell death (Newell, et al. PNAS 90 (3) 1127-1131 1993). Products of bacteria, viruses, and parasites cause cell surface expression of MHC class II invariant peptide (CLIP) in the groove of MHC class II and, most likely, MHC class I, over time through cross presentation. Because CLIP is a highly conserved self peptide, no traditional CD4 T cell can recognize CLIP directly in the groove of MHC class II because any CD4 that could have recognized the molecule would have been deleted in the thymus.

It has now been discovered that CLIP in the groove of MHC class II on a cell of the mucosal system protects the cell from cell death, for instance by preventing it from being recognized by conventional CD4 or CD8 T cells. Therefore, the invention in some aspects is a method for preventing cell death by the addition of CLIP to MHC to protect the cells from dying, and thus to protect the integrity of the mucosal cell wall.

These discoveries have important implications in the treatment of disorders of the mucosal system, including the gastrointestinal system such as autoimmune disease and infectious disease. A disorder of the mucosal system is a disruption in normal functioning of the mucosal system. The mucosal system, as used herein, refers to the tissue lining the mucosal membranes of the body, including for instance, the mouth, the nose, the gastrointestinal system (including for example, the esophagus, the stomach, the intestine, the colon, and the anus), the cervix, the vagina, and the uterus. A disorder of the gastrointestinal system is a disruption in normal functioning of the gastrointestinal system. Preferably the disruption in the mucosal system or gastrointestinal system functioning is associated with abnormal cell death of mucosal cells such as epithelial cells lining the cell walls of the system or the endothelial cells of the local blood vessels integrated in the mucosal system. The epithelial cells in the mucosal system form the mucosal epithelium, and are typically MHC positive. The endothelial cells of the local blood vessels are induced to express MHC under certain conditions. A CLIP molecule expressing cell is a cell that has MHC class I or II on the surface and includes a CLIP molecule within that MHC. Such cells include, for example, intestinal epithelial cells, endothelial cells, epithelial cells lining the uterine wall and the cervix wall, and skin cells.

Many therapies to block autoimmune involve eliminating or inhibiting B cells. No one knows the mechanism by which these B cell depleting therapies make people better. As described in co-pending U.S. Ser. No. 12/011,643 filed Jan. 28, 2008, now U.S. Pat. No. 8,557,764, issued Oct. 15, 2013, entitled METHODS OF MODULATING IMMUNE FUNCTION, and naming M. Karen Newell, Evan Newell and Joshua Cabrera as inventors, antigen non-specifically activated human B cells were treated with anti-CLIP antibodies and subjected to flow cytometry. It was found that the antigen-non-specifically activated B cells express cell surface CLIP. Thus, the inventors of U.S. Pat. No. 8,557,764 recognized that B cell surface expression of CLIP ultimately resulted in B cells that can present self antigens (antigens that load into the CLIP binding site) to Th1 cells, resulting in autoimmune disease.

A properly functioning immune system must discriminate between self and non-self. Failure of this process causes destruction of cells and tissues of the body in the form of autoimmune disease. Recognition of antigen in the thymus deletes some potentially self-reactive T cells from the repertoire. The process of antigen-specific T cell death in the thymus is commonly referred to as "negative" selection. The $CD4^+$ or $CD8^+$ T cells that recognize self MHC class I or MHC class II plus self antigen (like CLIP) will be deleted in the thymus. Those that could recognize CLIP and someone else's MHC class I or class II will not have been deleted. The cells that meet all of the survival criterion, e.g. appropriate recognition of antigen and either MHC class I for the developing $CD8^+$ T or MHC class II for the developing $CD4^+$ T cell travel to other regions of the body.

According to our invention, if an MHC molecule on an epithelial or endothelial cell of a mucosal tract is associated with CLIP, the cell will be protected from cell death. In order to reduce self-cell death in a subject having autoimmune disease, the self cells ordinarily targeted for destruction in autoimmune disease can be treated to express CLIP in the context of MHC, such that they are protected from destruction. This may be accomplished by treating the subject with a CLIP inducer to promote expression of the CLIP on the cell surface. The CLIP inducer is administered orally to the subject in order to deliver the active agent directly to the target cells of the mucosal tract.

A CLIP inducing agent as used herein refers to a compound that results in increased CLIP molecule presentation on the cell surface in the context of MHC. CLIP inducing agents include, for instance, CLIP expression vectors and CLIP activators. A CLIP expression vector is a vector that when administered to the cells causes production of a CLIP molecule protein. The CLIP molecule protein may be CD74, for instance. In the case that CD74 is produced it is desired that the CD74 be produced in the cell such that it can be processed intracellularly to produce a CLIP associated with MHC. Alternatively it may be processed in other cells that are capable of secreting it such that CD74 protein is capable of interacting with MHC on the surface. The expression vector may also produce a CLIP peptide either intracellularly or extracellularly. CLIP activators include for instance exogenous CLIP, palmitoylated protein or PAM, and an anti-CD40 or CD40L molecule in combination with IL-4.

Alternatively in our model, if an MHC molecule on an epithelial or endothelial cell of a mucosal tract is devoid of CLIP, the cell will be susceptible to MHC mediated cell death.

The CLIP molecule, as used herein, refers to intact CD74 (also referred to as invariant chain), as well as the naturally occurring proteolytic fragments thereof. CLIP is one of the naturally occurring proteolytic fragments thereof. The function of the CLIP molecule in this invention is mainly as an MHC class I or MHC class II chaperone and protective shield. MHC class II molecules are heterodimeric complexes that present foreign antigenic peptides on the cell surface of antigen-presenting cells (APCs) to $CD4^+$ T cells. MHC class II synthesis and assembly begins in the endoplasmic reticulum (ER) with the non-covalent association of the MHC a and chains with trimers of CD74. CD74 is a non-polymorphic type II integral membrane protein; murine CD74 has a short (30 amino acid) N-terminal cytoplasmic tail, followed by a single 24 amino acid transmembrane region and an ~150 amino acid long lumenal domain. Three MHC class II $\alpha\beta$ dimers bind sequentially to a trimer of the CD74 to form a nonameric complex $(\alpha\beta Ii)3$, which then exits the ER. After being transported to the trans-Golgi, the $\alpha\beta Ii$ complex is diverted from the secretory pathway to the endocytic system and ultimately to acidic endosome or lysosome-like structures called MHC class I or II compartments.

The N-terminal cytoplasmic tail of CD74 contains two extensively characterized dileucine-based endosomal targeting motifs. These motifs mediate internalization from the plasma membrane and from the trans-Golgi network. In the endocytic compartments, the CD74 chain is gradually proteolytically processed, leaving only a small fragment, the class II-associated CD74 chain peptide (CLIP), bound to the released $\alpha\beta$ dimers. The final step for MHC class II expression requires interaction of $\alpha\beta$-CLIP complexes with another class II-related $\alpha\beta$ dimer, called HLA-DM in the human system. This drives out the residual CLIP, rendering the $\alpha\beta$ dimers ultimately competent to bind antigenic peptides, which are mainly derived from internalized antigens and are also delivered to the endocytic pathway. The peptide-loaded class II molecules then leave this compartment by an unknown route to be expressed on the cell surface and surveyed by $CD4^+$ T cells.

The invention involves methods for treating a subject. A subject shall mean a human or vertebrate mammal including but not limited to a dog, cat, horse, goat and primate, e.g., monkey. Thus, the invention can also be used to treat diseases or conditions in non human subjects. Preferably the subject is a human.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

When used in combination with the therapies of the invention the dosages of known therapies may be reduced in some instances, to avoid side effects.

The CLIP inducer can be administered in combination with other therapeutic agents and such administration may be simultaneous or sequential. When the other therapeutic agents are administered simultaneously they can be administered in the same or separate formulations, but are administered at the same time. The administration of the other therapeutic agent and the CLIP inducer can also be temporally separated, meaning that the therapeutic agents are administered at a different time, either before or after, the administration of the CLIP inducer. The separation in time between the administration of these compounds may be a matter of minutes or it may be longer. For instance the CLIP inducer may be administered in combination with an antibody.

According to an embodiment of the invention, the methods described herein are useful in inhibiting the development of a gastrointestinal autoimmune disease in a subject by administering a CLIP inducer to the subject. Thus, the methods are useful for such autoimmune diseases as Crohn's disease, ulcerative colitis, inflammatory bowel disease, and celiac disease.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions. The methods of the invention are particularly useful in the treatment of gastrointestinal autoimmune diseases but are also useful in treating systemic autoimmune diseases that have a gastrointestinal component, such as scleroderma, as long as the therapy is delivered to the gut.

The CLIP inducers can also be administered orally to a subject having a gastrointestinal disorder such as that caused by infections. For instance *H Pylori* and HIV infection both cause damage to the gastrointestinal tract. Such damage can be avoided by administering to subjects infected with *H pylori* or HIV a CLIP inducer. The therapeutic agent is delivered mucosally (orally is preferred for delivery to the gastrointestinal system), such that it is exposed to the cells of the gastrointestinal tract. Systemic therapy for infections such as *H pylori* and HIV involve administering an inhibitor of CLIP. Therefore, while the subject is administered an oral dose of a CLIP inducer, the subject may also be treated systemically with a CLIP inhibitor.

A CLIP inhibitor as used herein is any molecule that reduces the association of a CLIP molecule with MHC by binding to the MHC and blocking the CLIP-MHC interaction. The CLIP inhibitor may function by displacing CLIP from the surface of a CLIP molecule expressing cell. CLIP inhibitors include peptides and small molecules that can replace CLIP. In some embodiments the CLIP inhibitor is a peptide. A number of peptides useful for displacing CLIP molecules are described in U.S. patent application Ser. No. 12/508,543 (publication number US-2010-0166782-A1); U.S. Ser. No. 12/739,459 (publication number US 2011-0118175 A1) and U.S. Ser. No. 12/508,532 (publication number US-2010-

0166789-A1). For instance a number of these peptides are "thymus nuclear protein (TNP)" peptides.

In some instances the peptides may be mixed with cystatin A and/or histones and in other instances the composition is free of cystatin A or histones. Histone encompasses all histone proteins including HI, H2A, H2B, H3, H4 and H5.

The peptide may be cyclic or non-cyclic. Cyclic peptides in some instances have improved stability properties. Those of skill in the art know how to produce cyclic peptides.

The peptides may also be linked to other molecules. The two or more molecules may be linked directly to one another (e.g., via a peptide bond); linked via a linker molecule, which may or may not be a peptide; or linked indirectly to one another by linkage to a common carrier molecule, for instance.

Thus, linker molecules ("linkers") may optionally be used to link the peptide to another molecule. Linkers may be peptides, which consist of one to multiple amino acids, or non-peptide molecules. Examples of peptide linker molecules useful in the invention include glycine-rich peptide linkers (see, e.g., U.S. Pat. No. 5,908,626), wherein more than half of the amino acid residues are glycine. Preferably, such glycine-rich peptide linkers consist of about 20 or fewer amino acids.

The peptide for instance, may be linked to a PEG molecule. Such a molecule is referred to as a PEGylated peptide.

The peptides useful herein are isolated peptides. As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). The isolated peptides may be substantially pure and essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems. In some embodiments, the peptide is a synthetic peptide.

The term "purified" in reference to a protein or a nucleic acid, refers to the separation of the desired substance from contaminants to a degree sufficient to allow the practitioner to use the purified substance for the desired purpose. Preferably this means at least one order of magnitude of purification is achieved, more preferably two or three orders of magnitude, most preferably four or five orders of magnitude of purification of the starting material or of the natural material. In specific embodiments, a purified thymus derived peptide is at least 60%, at least 80%, or at least 90% of total protein or nucleic acid, as the case may be, by weight. In a specific embodiment, a purified thymus derived peptide is purified to homogeneity as assayed by, e.g., sodium dodecyl sulfate polyacrylamide gel electrophoresis, or agarose gel electrophoresis.

The active agents of the invention are administered to the subject in an effective amount for treating disorders such as autoimmune disease. An "effective amount", for instance, is an amount necessary or sufficient to realize a desired biologic effect. An effective amount for treating autoimmune disease may be an amount sufficient to prevent or inhibit a decrease in $T_H$ cells compared to the levels in the absence of treatment. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another therapeutic, for instance, an anti-autoimmune agent a sub-therapeutic dosage of either or both of the molecules may be used. A "sub-therapeutic dose" as used herein refers to a dosage which is less than that dosage which would produce a therapeutic result in the subject if administered in the absence of the other agent.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be non-toxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration. The present invention involves administration of the therapeutic compounds orally.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Therapeutic formulations of the active compounds may be prepared for storage by mixing an active compound having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

A peptide, for instance, may be administered directly to a cell or a subject, such as a human subject alone or with a suitable carrier. Alternatively, a peptide may be delivered to a cell in vitro or in vivo by delivering a nucleic acid that expresses the peptide to a cell. Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

The active compound of the invention may also be expressed directly in mammalian cells using a mammalian expression vector. Such a vector can be delivered to the cell or subject and the peptide expressed within the cell or subject. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the α-fetoprotein promoter.

As used herein, a "vector" may be any of a number of nucleic acid molecules into which a desired sequence may be inserted by restriction and ligation for expression in a host cell. Vectors are typically composed of DNA although RNA vectors are also available. Vectors include, but are not limited to, plasmids, phagemids and virus genomes. An expression vector is one into which a desired DNA sequence may be inserted by restriction and ligation such that it is operably joined to regulatory sequences and may be expressed as an RNA transcript.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Effects of LPS, MKR.4 and Anti-MHC Class II Antibody Treatment on CRL-5822 Cells In order to determine whether the displacement of CLIP with peptide in the absence or presence of a TLR ligand resulted in induction of Class II associated death in CRL-5822 the following experiment was performed.
Methods
The media was removed from a flask of CRL-5822 using a sterile glass pipet and vacuum and 1.5 mL of accutase was added to the flask and placed in incubator for 20 minutes
The cells were washed with 3 mL of PBS and transferred to a sterile 15 mL conical tube and centrifuged for 5 minutes @1000 rpm
The supernatant was removed with sterile glass pipet and vacuum and the pellet resuspended in 5 mL of PBS
A cell count was performed using the TC-10 automated counter
Loaded 10 ul of cell suspension+10 ul of trypan blue into disposable counting slide
Loaded slide into the TC-10
Count
Live: $3.54*10^4$ cells/mL*5 mL=177,000 cells total
177,000/9 wells (8 wells in experiment+1 to maintain culture)=19,666 cells/well (flask).
The 5 mL of cell suspension was centrifuged for 5' at 1000 rpm, the pellet was resuspended in 9 mL of 10% FBS RPMI
1 mL of the cell suspension was added to a T-25 flask that had 4 mL of media in it and placed in the incubator.
After culture 1 mL of the cell suspension was added to each well (8 wells in a labeled 24 well plate)
A fresh vial of MKR.4 was resuspended in sterile DMSO
7 mg of peptide was used to make a 5 mg/mL stock
7 mg/mL=5 mg/mL=1.4 mL of DMSO
The peptide was added into 1.4 mL of DMSO, under the hood to maintain sterility
Once all of the peptide was dissolved, 200 ul aliquots were made
8 wells were set up for the experiment with no treatment, with LPS, with MKR.4 peptide, with MKR.4 peptide+LPS and with or without addition of purified Anti Class-II (HLA-DR,DP,DQ) treatment in the amounts listed below.
Stock Concentrations:
LPS: 1 ug/mL (Sigma-Aldrich, St. Louis, Mo.)
MKR.4: 2.5 ug/mL (SEQ ID NO 2: ANS GFR IMA VLA SGG QY)
LPS:
(x) (5 mg/mL stock)=(1 ug/mL) (1 mL)
x=0.2 ul*8 wells=1.6 ul+8.4 ul PBS=10 ul/8 wells=1.25 ul mixture/well MKR.4:
  (x) (5 mg/mL stock)=(2.5 ug/mL) (1 mL)
    x=0.5 ul*4 wells=2 ul MKR.4+8 ul PBS=2.5 ul mixture/well
Anti MHC Class II (eBioscience, San Diego, Calif.)
  Treat at 5 ug/mL
  Stock is at 1 mg/mL
  (x) (1 mg/mL)=(5 ug/mL) (1 mL)
    x=5 ul/well
Treatment Procedure LPS was administered to activate the cells and induce CLIP expression. MKR.4 was added to select wells 24 hours after cell activation. The cells were incubated with MKR.4 for 2 hours. Then fresh media with or without Anti MHC Class II was added. 24 hours after Anti MHC Class II was added to the wells viability counts were performed.

Results:

The cell counts are presented below. The results were incorporated into a graph and depicted in FIG. 1.

Counts
No Treatment 1:2 in 1 mL
8/0
11/4
14/2
13/5
Total Live: $0.23*10^6$
Total Dead: $0.06*10^6$
LPS 1:2 in 1 mL
9/2
12/5
12/1
10/6
Total Live: $0.22*10^6$
Total Dead: $0.07*10^6$
MKR.4 1:2 in 1 mL
15/3
13/5
22/3
13/2
Total Live: $0.32*10^6$
Total Dead: $0.07*10^6$
MKR.4+LPS 1:2 in 1 mL
10/5
17/7
8/2
13/6
Total Live: $0.24*10^6$
Total Dead: $0.10*10^6$
No Treatment+Anti Class II 1:2 in 1 mL
8/6
10/5
11/4
9/3
Total Live: $0.19*10^6$
Total Dead: $0.09*10^6$
MKR.4+Anti Class II 1:2 in 1 mL
14/5
16/10
21/5
14/4
Total Live: $0.33*10^6$
Total Dead: $0.12*10^6$
LPS+Anti Class II 1:2 in 1 mL
11/9
20/6
10/7
17/15
Total Live: $0.29*10^6$
Total Dead: $0.19*10^6$
LPS+MKR.4+Anti Class II 1:2 in 1 mL
4/5
3/3
5/7
4/5
Total Live: $0.08*10^6$
Total Dead: $0.10*10^6$ Example 2

Effects of CpG, MKR.4, and Anti MHC Class II Antibody Treatment on C57BL/6 Splenocytes and CRL-5822 Cells In order to determine whether the displacement of CLIP with peptide in the absence or presence of a TLR ligand resulted in induction of Class II associated death in C57BL/6 Splenocytes and CRL-5822 the following experiment was performed.

Methods:
CRL-5822 were Prepared as Follows:
  Removed the media from a flask of CRL-5822 using a sterile glass pipet and vacuum
  Added 1.5 mL of accutase to the flask and placed in incubator for 20 minutes
  Washed with 3 mL of PBS
  Transferred all to a sterile 15 mL conical tube
  Centrifuged for 5'@1000 rpm
  Removed supernatant with sterile glass pipet and vacuum
  Resuspended in 3 mL of PBS
  Performed a hemacytometer count indicating: $1.14*10^6$ cells total of CRL-5822 cells
  $1.14*10^6/8$ wells+2 wells for culture maintenance=10 wells
    $1.14*10^6/10$ wells=11,400 cells per well
  Centrifuged the 3 mL of cell suspension for 5' at 1000 rpm
  Resuspended pellet in 10 mL of 10% FBS RPMI
  1 mL of this was added to 2 wells in a 12-well plate added 1 mL of fresh 10% FBS RPMI to each well to bring the total volume up to 2 mL.
C57BL/6 were Prepared as Follows:
  A spleen from a C57BL/6 mouse was placed in a cell strainer in a petri dish with 6 mL of PBS
  The spleen was mashed to produce a cell suspension
  The PBS splenocyte cell suspension was transferred into a labeled 15 mL conical tube and centrifuged for 5 minutes at 1000 rpm
  The pellet was resuspended in 1 mL of PBS
  Geys was prepared to lyse the red blood cells
    7 mL of DI H20
    0.5 mL of Geys B
    0.5 mL of Geys C
    weighed out 0.07 mg of NH4Cl
    Mixed the 0.07 mg of NH4Cl with 2 mL of Geys A
    Transferred the dissolved solution to a 15 mL conical tube with the H20, Geys B, and Geys C
  3 mL of the Geys solution was added to the 1 mL of PBS cell suspension, mixed well and placed on ice for 1 minute (frequently inverted solution in tube on ice during the 1 minute)

The mixture was centrifuged for 5 minutes at 1000 rpm, washed with 5 mL of PBS, centrifuged for 5 minutes at 1000 rpm and resuspended in 10 mL of PBS A hemacytometer count was performed: $99.0*10^6$ cells total ($9.9*10^6$ cells/mL) plate $4*10^6$ cells per well*8 wells=32 million; $32*10^6/9.9*10^6$=3.23 mL of this suspension needed to obtain $32*10^6$ cells Centrifuged 3.23 mL of the suspension for 5 minutes at 1000 rpm and resuspended the pellet in 8 mL of 5% FBS RPMI 1 mL of suspension was added to each well (12-well plate)

Added another 2 mL of 5% FBS RPMI to each well to bring the final volume up to 3 mL 8 wells were set up for the experiment for each cell type (CRL-5822 and C57BL/6) with no treatment, with CpG, MKR.4 peptide, with MKR.4 peptide+CpG and with or without addition of purified Anti Class-II (HLA-DR,DP,DQ) treatment in the amounts listed below.

Stock Concentrations:
CPG: 1 mg/mL (SEQ ID NO 3: 5'-tcgtcgttttgtcgttttgtcgtt-3', purchased from InVitrogen)
MKR.4: 5 mg/mL (SEQ ID NO 2: ANS GFR IMA VLA SGG QY)
CRL-5822
CpG:
  (x) (1 mg/mL stock)=(1 ug/mL) (2 mL)
    x=2 ul
MKR.4:
  (x) (5 mg/mL stock)=(2.5 ug/mL) (2 mL)
    x=1 ul
Anti MHC Class II
  Treat at 5 ug/mL
  Stock is at 1 mg/mL
  (x) (1 mg/mL)=(5 ug/mL) (2 mL)
    x=10 ul/well
C57BL/6
CpG:
  (x) (1 mg/mL stock)=(5 ug/mL) (3 mL)
    x=15 ul
MKR.4:
  (x) (5 mg/mL stock)=(5 ug/mL) (3 mL)
    x=3 ul
Anti MHC Class II
  Treat at 5 ug/mL
  Stock is at 1 mg/mL
  (x) (1 mg/mL)=(5 ug/mL) (3 mL)
    x=15 ul/well Treatment Procedure CpG was administered to activate the cells and induce CLIP expression. MKR.4 was added to select wells 24 hours after cell activation. The cells were incubated with MKR.4 for 2 hours. Then fresh media with or without Anti MHC Class II was added. 24 hours after Anti MHC Class II was added to the wells viability counts were performed.

Figure 2:
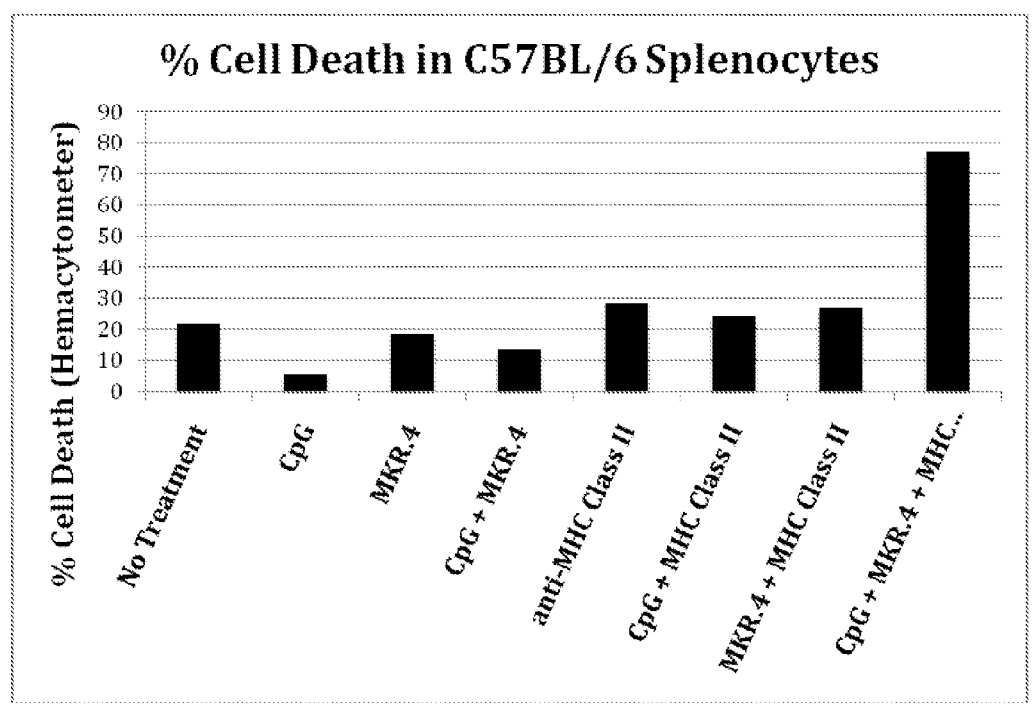
FIG. 2 depicts % cell death in either untreated C57BL/6 splenocyte cells or cells treated with CpG, MKR.4, MKR.4+CpG, anti-MHC class II antibody, CpG+anti-MHC class II antibody, MKR.4+anti-MHC class II antibody or MKR.4+CpG+anti-MHC class II antibody.

Results:

The cell counts are presented below. The results for C57BL/6 were incorporated into a graph and depicted in FIG. 2.

CRL-5822 Counts
No Treatment 1:2 in 1 mL
9/4
19/4
7/2
10/3
Total Live: $0.23*10^6$
Total Dead: $0.07*10^6$
CpG 1:2 in 1 mL
12/6
21/3
24/3
13/2
Total Live: $0.35*10^6$
Total Dead: $0.07*10^6$
MKR.4 1:2 in 1 mL
13/3
10/4
12/2
12/7
Total Live: $0.24*10^6$
Total Dead: $0.08*10^6$
MKR.4+CpG 1:2 in 1 mL
10/5
10/4
13/4
17/4
Total Live: $0.25*10^6$
Total Dead: $0.09*10^6$
No Treatment+Anti Class II 1:2 in 1 mL
5/14
8/18
6/13
7/22
Total Live: $0.13*10^6$
Total Dead: $0.34*10^6$
MKR.4+Anti Class II 1:2 in 1 mL
5/18
4/12
13/12
5/13
Total Live: $0.14*10^6$
Total Dead: $0.28*10^6$
CpG+Anti Class II 1:2 in 1 mL
20/1
21/5
16/2
15/6
Total Live: $0.36*10^6$
Total Dead: $0.07*10^6$
CpG+MKR.4+Anti Class II 1:2 in 1 mL
15/10
16/8
9/10
5/7
Total Live: $0.23*10^6$
Total Dead: $0.18*10^6$
C57BL/6 Counts
No Treatment 1:5 in 1 mL
13/3
13/3
13/4
11/4
Total Live: $0.63*10^6$
Total Dead: $0.18*10^6$
CpG 1:5 in 1 mL
20/0
28/3
31/2
21/1
Total Live: $1.25*10^6$
Total Dead: $0.08*10^6$ MKR.4 1:2 in 1 mL
21/5
26/6
16/5
24/4
Total Live: $0.44*10^6$
Total Dead: $0.10*10^6$
MKR.4+CpG 1:5 in 1 mL
26/2
34/4
18/3
30/8
Total Live: $1.35*10^6$
Total Dead: $0.21*10^6$
No Treatment+Anti Class II 1:2 in 1 mL
28/9
27/12
19/8
31/13
Total Live: $0.53*10^6$
Total Dead: $0.21*10^6$
MKR.4+Anti Class II 1:2 in 1 mL
10/3
11/2
12/6
10/5
Total Live: $0.22*10^6$
Total Dead: $0.08*10^6$
CpG+Anti Class II 1:5 in 1 mL
12/4
10/5
18/8
24/4
Total Live: $0.80*10^6$
Total Dead: $0.26*10^6$
CpG+MKR.4+Anti Class II 1:5 in 1 mL
6/13
4/24
8/15
3/18
Total Live: $0.26*10^6$
Total Dead: $0.88*10^6$ Example 3

Figure 3:
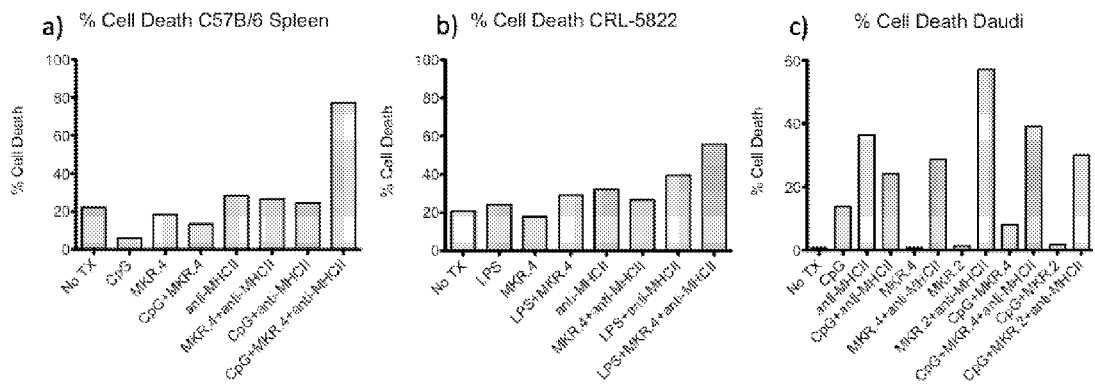
FIGS. 3A-3C are a set of graphs depicting changes in cell death resulting from displacement or lack thereof of CLIP from MHCII. The cells (spleen cells obtained from a 12 week old male C57B/6 mouse 93a), CRL-5822 gastric epithelial cells (3b) and Daudi B cell lymphoblast cells (3c)) were treated with CpG oligonucleotide, MKR.4 (3a and 3b) or MKR.4 and MKR.2 (3c) and Anti-MHCII and the cells were examined for viability.

Effects of CpG, MKR.4 or MKR.2, and Anti MHC Class II Antibody Treatment on C57BL/6 Splenocytes, CRL-5822 Cells and Daudi B Cell Lymphoblast Cells In order to determine the effects of CLIP displacement on MHC Class II mediated cell death, the following experiments were performed on three different types of cells and with two different peptides.
Methods:
C57BL/6 Splenocytes were Prepared as Follows:
A spleen from a 12 week old male C57B/6 mouse was placed in a cell strainer in a petri dish and mashed into a single cell suspension.
GEYS buffer
  7 mL of DI H20
  2 mL of GEYS A
  0.5 mL of GEYS B
  0.5 ML of GEYS C
  0.07 mL of NH4Cl
Cells were resuspended in 1 mL of PBS and 3 mL of complete GEYS buffer and incubated on ice for 1 minute inverting every 15 seconds. After incubation cells were washed with PBS.
Cells were counted with trypan blue on a hemacytometer.
Cells were pated at $1\times10^6$ cells/mL in 3 mL of media.
Cells were treated as in FIG. 3a with the following concentrations:
  CpG, SEQ ID NO 3=5 µg/mL at T=0
  MKR.4, SEQ ID NO 2=5 µg/mL at T=24 hours
  Anti-MHC class II=5 µg/mL at T=26 hours
  24 hours after the anti-MHCII was added the cells were counted with trypan blue to determine viability and number.
CRL-5822 were Prepared as Follows:
CRL-5822 gastric epithelial cells were acquired from ATCC.
Cells were grown to confluence in a T-75 flask.
Cells were removed from the flask using Accutase and their number and viability was determined via trypan blue exclusion on a hemacytometer.
Cells were plated at 19,666 cells/ml in 1 mL.
Cells were allowed to stick to the plate and then treated as in FIG. 3b with the following concentrations:
  CpG, SEQ ID NO 3=5 µg/mL at T=0
  MKR.4, SEQ ID NO 2=5 µg/mL at T=24 hours
  Anti-MHCII=5 µg/mL at T=26 hours
  24 hours after the anti-MHC class II was added the cells were counted with trypan blue to determine viability and number.
Daudi B Cell Lymphoblast Cells were Prepared as Follows:
Daudi B cell lymphoblast cell line was acquired from ATCC. Cells were grown to confluence in a T-75 flask.
Cells were removed from the flask using Accutase and their number and viability was determined via trypan blue exclusion on a hemacytometer.
Cells were plated at $0.5\times10^6$ cells/ml in 2 mL.
Cells were allowed to stick to the plate and then treated as in FIG. 3b with the following concentrations:
  CpG, SEQ ID NO 3=5 µg/mL at T=0
  MKR.4, SEQ ID NO 2=5 µg/mL at T=24 hours
  MKR.2 (SKMRMATPLLMQALY, SEQ ID NO: 4)=5 ug/mL at T=24 hours
  Anti-MHC Class II=5 µg/mL at T=26 hours
  24 hours after the anti-MHCII was added the cells were counted with trypan blue to determine viability and number.
Treatment Procedure
CpG was administered to activate the cells and induce CLIP expression. MKR.4 or MKR.2 was added to select wells 24 hours after cell activation. The cells were incubated with MKR.4 or MKR.2 for 2 hours. Then fresh media with or without Anti MHC Class II was added. 24 hours after Anti MHC Class II was added to the wells viability counts were performed.
Results:
The data is shown in FIG. 3. The experiments show that displacement of CLIP from MHC class II, followed by triggering through MHC class II engagement, results in cell death. However, if CLIP is not displaced from MHC class II, signaling through MHC class II does not increase cell death. Thus, the cell surface CLIP is protective of the cells and displacement renders the cells susceptible to cell death. The activity is conserved between lymphoid cells and gastric epithelium.

Example 4

Effects of CpG, MKR.4, and Anti MHC Class II Antibody Treatment on Antibody Production in C57BL/6 Splenocytes In order to determine the consequences of CLIP displacement on mucosal immunity and inflammation the following experiment was performed.

Methods:
A spleen from a 12 week old male C57B/6 mouse was placed in a cell strainer in a petri dish and mashed into a single cell suspension.

GEYS buffer
  7 mL of DI H20
  2 mL of GEYS A
  0.5 mL of GEYS B
  0.5 ML of GEYS C
  0.07 mL of NH4Cl Cells were resuspended in 1 mL of PBS and 3 mL of complete GEYS buffer and incubated on ice for 1 minute inverting every 15 seconds. After incubation cells were washed with PBS.

Cells were counted with trypan blue on a hemacytometer. Cells were pated at $1 \times 10^6$ cells/mL in 10 mL of media.

Cells were treated in FIGS. 4a and b with the following concentrations:
  CpG, SEQ ID NO 3=5 μg/mL at T=0
  MKR.4, SEQ ID NO. 2=5 μg/mL at T=48 hours
  Anti-MHC class II=5 μg/mL at T=50 hours 24 hours after the anti-MHCII was added the cells were transferred to 15 mL conical tubes and centrifuged to pellet the cells. The supernatant was removed and the quantity of IgA (4a) and IgG$_2$ (4b) was measured using ELISA kits from Bethyl Laboratories Inc. (IgA E99-103 and IgG$_{2c}$ E99-136).

Treatment Procedure

CpG was administered to activate the cells and induce CLIP expression. MKR.4 was added to select wells 48 hours after cell activation. The cells were incubated with MKR.4 for 2 hours. Then fresh media with or without Anti MHC Class II was added. 24 hours after Anti MHC Class II was added to the wells the quantity of IgA and IgG$_{2c}$ was measured.

Figure 4:
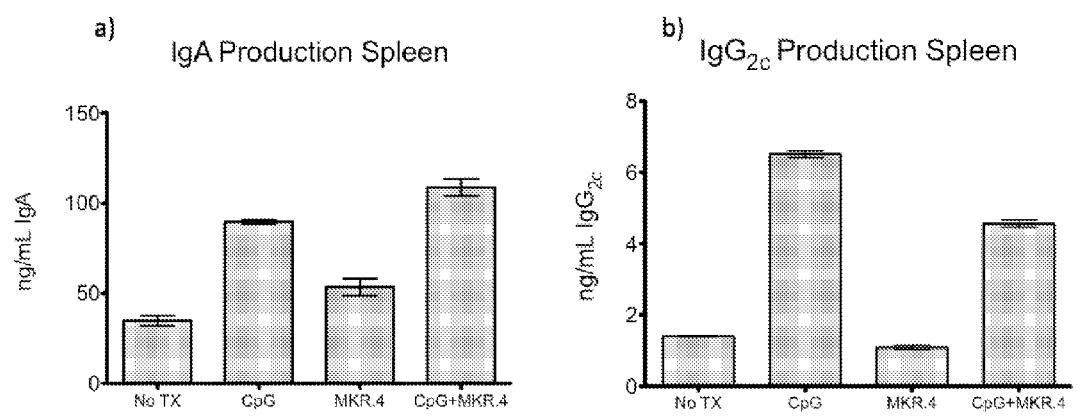
FIGS. 4A and 4B are a set of graphs depicting antibody levels in response to treatment. In order to determine the consequences of CLIP displacement on mucosal immunity and inflammation a spleen from a 12 week old male C57B/6 mouse was used to generate cells that were then treated with CpG oligonucleotide, MKR.4 and Anti-MHCII. The quantity of IgA (4a) and IgG2c (4b) was measured.

Results:

The data is shown in FIG. 4. The experiments show that displacement of CLIP from MHC class II results in changes in the type of antibody isotype that is secreted. FIG. 4a shows the levels of IgA and FIG. 4b shows the levels of IgG$_{2c}$. These changes include increased IgA. IgA is important in mucosal immunity and may be a mediator of gastrointestinal diseases. In addition, CLIP displacement results in decreased IgG$_{2c}$. IgG$_{2c}$ has been shown to be up regulated in chronic inflammatory diseases, decreasing IgG$_{2c}$ production may ameliorate some of the symptoms associated with these diseases.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

---

What is claimed is:

1. A method of treating a subject having inflammatory bowel disease, comprising administering to the subject a CLIP-inducing agent in an effective amount to treat the inflammatory bowel disease.

2. The method of claim 1, wherein the inflammatory bowel disease is Crohn's disease.

3. The method of claim 1, wherein the inflammatory bowel disease is ulcerative colitis.

4. The method of claim 1, wherein the CLIP-inducing agent is exogenous CLIP.

5. The method of claim 4, wherein the exogenous CLIP comprises an amino acid sequence comprising a region consisting essentially of SEQ ID NO:1.

6. The method of claim 1, wherein the CLIP-inducing agent is a CLIP expression vector.

7. The method of claim 1, wherein the CLIP-inducing agent is a CLIP activator selected from the group consisting of palmitoylated protein or PAM (palmitoyl-3-Cys-Ser-(Lys)(4)) and an anti-CD40 or anti-CD40L molecule in combination with IL-4.

8. The method of claim 1, wherein the CLIP-inducing inducing agent is administered orally to the subject.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Met Arg Met Ala Thr Pro Leu Leu Met
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 2

Ala Asn Ser Gly Phe Arg Ile Met Ala Val Leu Ala Ser Gly Gly Gln
1               5                   10                  15

Tyr

<210> SEQ ID NO 3
<211> LENGTH: 24
<212> TYPE: DNA
```

```
<213> ORGANISM: Artificial Sequence
<220> FEATURE:
<223> OTHER INFORMATION: Synthetic Oligonucleotide

<400> SEQUENCE: 3
tcgtcgtttt gtcgttttgt cgtt                                        24
```